US00PP34413P2

(12) United States Plant Patent
Hansen

(10) Patent No.: US PP34,413 P2
(45) Date of Patent: Jul. 5, 2022

(54) **X *MANGAVE* PLANT NAMED 'WINGMAN'**

(50) Latin Name: **x *Mangave* hybrid; *Manfreda* times *Agave***
Varietal Denomination: 'Wingman'

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,742

(22) Filed: Oct. 14, 2021

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Karen M Redden

(57) ABSTRACT

A new and unique x *Mangave* plant named 'Wingman' characterized by a medium mound of narrow, fleshy mostly flat foliage that is glaucous becoming shiny, with small flexible cream-colored marginal teeth that become firm and orangish-colored when mature. Foliage is mostly outwardly and medio-variegated. The outer margins are dark reddish-green, the inner portion is dark reddish green with grey-green undertones and the region between the margin and center is yellowish with dark red broken spots. The new plant is suitable for the garden or as a potted plant in the garden or home.

2 Drawing Sheets

Botanical classification: x *Mangave* hybrid; *Manfreda* times *Agave*.

Variety denomination: 'Wingman'.

STATEMENT REGARDING PRIOR DISCLOSURES UNDER 37 CFR 1.77(b)(6)

No plants of x *Mangave* 'Wingman' have been sold, by this name or any other name, in this country or anywhere in the world, nor has any disclosure of the new plant been made prior the filing date of this application.

BACKGROUND OF THE INVENTION

The present invention relates to the new and distinct x *Mangave* hybrid plant, x *Mangave* 'Wingman' that was discovered by the inventor at a wholesale perennial nursery in Zeeland, Mich., USA on May 28, 2019, as a whole-plant, streaked, variegated mutation of x *Mangave* 'Red Wing' U.S. Plant Pat. No. 31,459. The streaked form later stabilized into the current sport. Through trials at the same nursery the plant was assigned the breeder code 19-SP-MANG-847 through the evaluation process. The new plant has been successfully asexually propagated by removal of the basal offsets at the same nursery in Zeeland, Mich. The asexual propagation has been found to produce stable and identical plants that maintain all the unique characteristics of the original plant in multiple generations.

BRIEF SUMMARY OF THE INVENTION x *Mangave* 'Wingman' differs from its parents as well as all other *Manfreda, Agave* and x *Mangave* known to the applicant. The sport parent has a similar habit, but the new plant has foliage with a lighter colored center with the region between the center and the margin becoming yellowish with dark reddish spotting.

The nearest comparison plants are: 'Carnival' U.S. Plant Pat. No. 31,249, 'Center of Attention' U.S. Plant Pat. No. 33,630, 'Dragon Lady' U.S. Plant patent application Ser. No. 17/300,490, 'Kaleidoscope' U.S. Plant Pat. No. 28,614, 'Queen for a Day' U.S. Plant Pat. No. 32,711 and 'Pineapple Punch' U.S. Plant Pat. No. 32,041.

'Carnival' has broader and longer leaves and is larger in habit. 'Center of Attention' has foliage that is slightly longer and broader with more dark greyed-purple spotting on a more glaucous light greyed-green to greyed-purple background without the yellowish coloration between the margin and the center. 'Dragon Lady' has more sinuate and channeled leaves with Leaf centers that are variegated with creamy-yellow and cherry-red spots. 'Kaleidoscope' has broader and longer leaves and is larger in habit, reverse variegation with the lighter color in the center, and the purple spots are larger and more defined. 'Queen for a Day' has foliage that is broader than the new plant, slightly wavy and arching leaves that have olive-green centers and dark, purplish-grey foliage margins with larger and firmer marginal teeth. 'Pineapple Punch' has a larger habit with longer and broader foliage that has a yellowish variegated margin and the burgundy spotting is larger.

The new plant, 'Wingman', is unique from all the above cultivars and all *Agave*, x *Mangave* and *Manfreda* known to the inventor by the following combined traits:

1. Medium mound of glaucous foliage becoming shiny;
2. Leaves are variegated with dark reddish-green margins with small broken reddish spots, and dark reddish center having a greyed-green undertone, and the region between the margin and the center is yellowish with dark red broken spots;
3. Leaf margins have small, flexible, cream-colored marginal teeth;

4. Moderate to slow growth rate;
5. Foliage is upright to outwardly from central stem.

BRIEF DESCRIPTION OF THE DRAWING

The photograph of x *Mangave* 'Wingman' demonstrates the overall appearance of the new plant including the unique traits as a two-year-old plant grown in a container and then in a full-sun trial garden in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
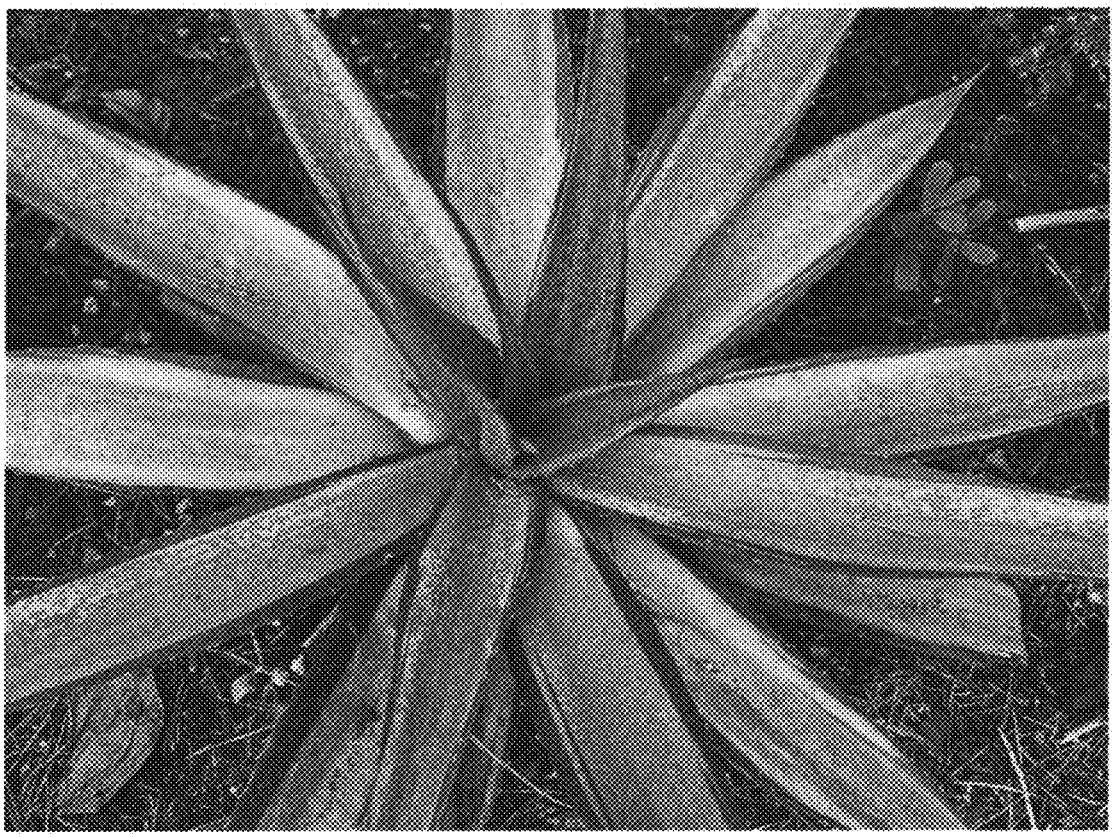
FIG. 1 shows a top view of the new plant.
Figure 2:
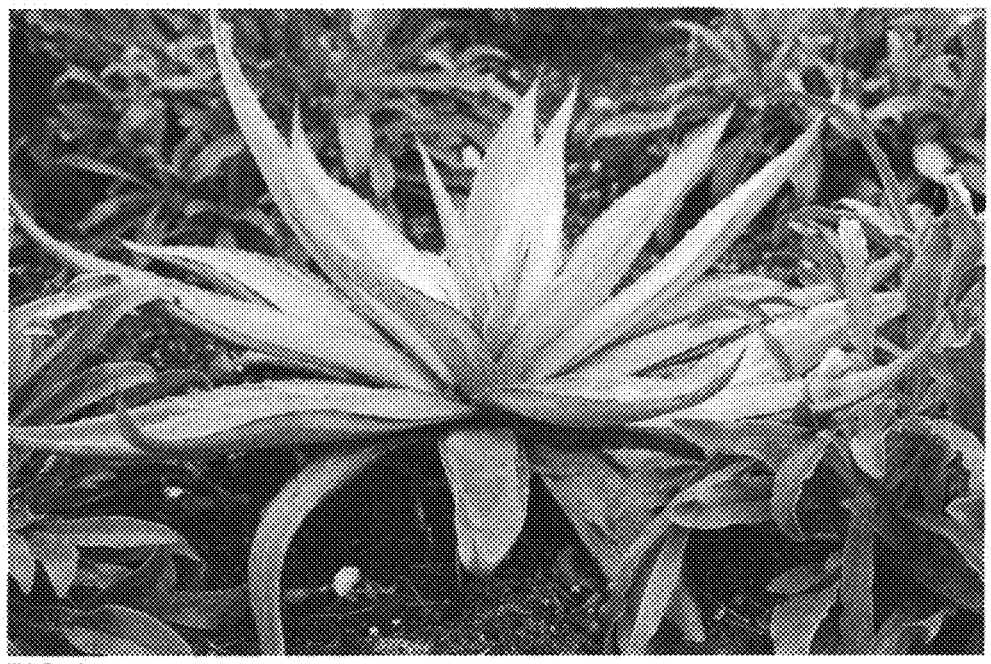
FIG. 2 shows a side view of the new plant.
Figure 3:
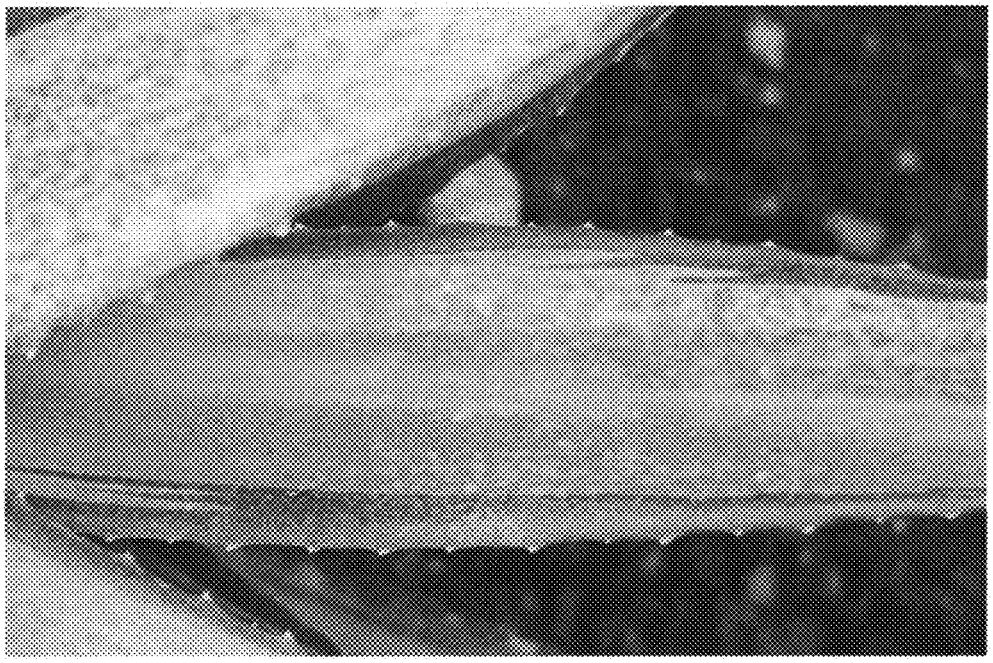
FIG. 3 shows a close-up of the leaf showing marginal teeth and broken dark red spotting.

The following descriptions and color references are based on the 2015 edition of The Royal Horticultural Society Colour Chart except where common dictionary terms are used. The new plant, x *Mangave* 'Wingman', has not been observed under all possible environments. The phenotype may vary slightly with different environmental conditions, such as temperature, light, fertility, moisture and maturity levels, but without any change in the genotype. The following observations and size descriptions are of a two-year-old plant in a commercial wholesale greenhouse and in a full-sun trial garden in Zeeland, Mich. with supplemental water and fertilizer as needed.

Parentage: A whole plant stabilized mutation of a streaked whole plant mutation of 'Red Wing';

Propagation: By sterile shoot-tip tissue culture; and removal of basal offsets;

Time to initiate roots from tissue culture: About 21 days;

Growth rate: Moderate to slow;

Crop time: About 18 to 24 weeks to finish in a 3.8-liter container from a 35 mm tissue culture growing at about 21° C.;

Rooting habit: Fleshy, lightly branching, with roots up to 30 cm long;

Root color: Nearest RHS 158C;

Plant shape and habit: Succulent herbaceous perennial with basal rosettes of about 29 leaves radially emerging outwardly from central stem prior to flowering, producing a radially-symmetrical, rounded mound;

Plant size: Foliage height about 24.0 cm tall from soil line to the top of the leaves and about 44.0 cm wide at the widest point about middle of the plant;

Foliage description: Gladiate; simple; sessile; bi-laterally symmetrical; sarcous; apex narrowly acute with terminal spine; base truncate; mostly flat with flat margins; margins finely dentate; glabrous and dull becoming slightly lustrous abaxial and adaxial; glaucous abaxial and adaxial;

Marginal teeth: With small flexible teeth that become firm with maturity; about 1.0 mm long and 2.0 mm wide at base; about 9.0 mm apart in center on mature leaves;

Terminal spine: Firm; to about 11.0 mm long and 2.0 mm wide at base; color nearest RHS 187B;

Leaf size: To about 24.8 cm long, about 4.0 cm wide toward base; center base about 9.0 mm thick at basal midrib; average about 21.0 cm long, 3.5 cm wide and 6.0 mm thick in longitudinal center;

Foliage fragrance: None observed;

Leaf number: About 29 per plant;

Leaf blade color:

*Adaxial* (*mature*).—In lower ultraviolet light nearest RHS 137A without spotting or blushing; longitudinal center approximate half between RHS N148A and RHS N148B with highly broken irregular spotting or blushing nearest RHS 187A and concentration dependent on intensity of ultraviolet light; longitudinal region between margin and center between RHS 151A and RHS 153D with spotting and blushing nearest RHS 187A and concentration dependent on intensity of ultraviolet light.

*Adaxial* (*mature*).—In higher ultraviolet light margin between RHS NN137A and RHS 187A; longitudinal center nearest RHS 187A with an undertone of nearest RHS 189A; region between center and margin leaf middle between RHS 181B and RHS 181A with undertone of nearest RHS 147B, and short random streaks of between RHS NN137A and RHS 187A extending from the margin, and distally nearest RHS 146D with slight spotting or blushing of nearest RHS 187C.

*Abaxial* (*mature*).—In lower ultraviolet light nearest RHS NN137B; longitudinal center approximate half between RHS 147C and RHS 145A; region between margin and longitudinal center between RHS 160B and RHS 146D.

*Adaxial* (*mature*).—In high ultraviolet light margin between RHS 139A and RHS NN137B with light blush or irregular spotting of nearest RHS 187B; longitudinal center approximate half between RHS 147C and RHS 145C with slight blush of nearest RHS 187C and region between longitudinal center and margin nearest RHS 153D with light blush of nearest RHS 187C.

*Adaxial* (*young*).—Margin nearest RHS NN137A with spots and slight blush of nearest RHS 187B, the longitudinal center approximate half between RHS 146D and RHS 147C with irregular broken spots and light blushing nearest RHS 187C, longitudinal region between margin and center between RHS 8B and RHS 160B with irregular broken spots and light blushing nearest RHS 187C.

*Abaxial* (*young*).—Margin nearest RHS 137B with moderate blushing of nearest RHS 187B, longitudinal center approximate half between RHS 146D and RHS 145A with minimal spotting of nearest RHS 187B, region between longitudinal center and margin between RHS 160B and RHS 8B with moderate spotting and moderate blushing of nearest RHS 187B.

*Marginal teeth.*—Nearest RHS 160D adaxial and abaxial when young, becoming nearest RHS 158A adaxial and abaxial with maturity and high light.

*Terminal spine.*—Proximally nearest RHS 187B, apical 1.0 mm nearest RHS 162D and distal one-third just anterior the apex nearest RHS 183C.

*Leaf interior cross section.*—Inner core or L3 histogenic region, corresponding to the longitudinal center is nearest RHS 137A, the L2 surrounds the L3 and is nearest RHS 11C, the L1 on the margin outside the L2 is between RHS 137A and RHS 136A.

Petiole: Leaves sessile;

Veins: Parallel; not distinct abaxial or adaxial;

Inflorescence description: The new plant has not yet flowered;

Fruit and seed: Not yet observed;

Disease resistance: x *Mangave* 'Wingman' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Wingman' as herein described and illustrated.

* * * * *